US012667475B1

(12) United States Patent
Lockart et al.

(10) Patent No.: US 12,667,475 B1
(45) Date of Patent: Jun. 30, 2026

(54) BRACE WITH RESISTANCE BAND

(71) Applicant: B.R.I.C.E.P. Devices, LLC,
Tallahassee, FL (US)

(72) Inventors: Brice W Lockart, Tallahassee, FL
(US); John Martelli, Pensacola, FL
(US)

(73) Assignee: B.R.I.C.E.P. Devices, LLC,
Tallahassee, FL (US)

( * ) Notice: Subject to any disclaimer, the term of this
patent is extended or adjusted under 35
U.S.C. 154(b) by 0 days.

(21) Appl. No.: 19/198,058

(22) Filed: May 4, 2025

Related U.S. Application Data

(63) Continuation-in-part of application No. 17/945,193,
filed on Sep. 15, 2022, now Pat. No. 12,303,417.

(51) Int. Cl.
*A61F 5/01* (2006.01)

(52) U.S. Cl.
CPC .... *A61F 5/0123* (2013.01); *A61F 2005/0137*
(2013.01); *A61F 2005/0169* (2013.01); *A61F*
*2005/0179* (2013.01)

(58) Field of Classification Search
CPC ...... A61F 2005/0137; A61F 2005/0167; A61F
2005/0169; A61F 2005/0179; A61F
5/0123; A61F 5/042; A61F 5/04; A61F
5/058; A61F 5/05841; A61F 5/05; A61F
5/05825; A61F 5/05858; A63B 21/0414;
A63B 21/0557; A63B 21/0552; A63B
21/055; A63B 21/0407; A63B 21/04;
A63B 23/0405; A63B 23/04; A63B
23/0494
See application file for complete search history.

(56) References Cited

U.S. PATENT DOCUMENTS

| | | | | |
|---|---|---|---|---|
| 4,606,542 | A * | 8/1986 | Segal | A63B 21/4025 |
| | | | | 482/124 |
| 5,203,754 | A * | 4/1993 | Maclean | A63B 21/4015 |
| | | | | 482/121 |
| 5,865,714 | A * | 2/1999 | Marlowe | A63B 21/4025 |
| | | | | 601/33 |
| 6,117,097 | A * | 9/2000 | Ruiz | A61F 5/0109 |
| | | | | 602/26 |
| 10,966,854 | B1 * | 4/2021 | Lockart | A61F 5/013 |
| 11,253,385 | B1 * | 2/2022 | Lockart | A61F 5/0123 |
| 12,303,417 | B1 * | 5/2025 | Lockart | A61F 5/0123 |
| 2006/0063651 | A1 * | 3/2006 | Sload | A63B 21/0004 |
| | | | | 482/124 |
| 2009/0312683 | A1 * | 12/2009 | Burns | A63B 23/0494 |
| | | | | 602/26 |

* cited by examiner

*Primary Examiner* — Camtu T Nguyen
(74) *Attorney, Agent, or Firm* — Peter Loffler

(57) ABSTRACT

A rehabilitation system for use with a limb brace assists a
user in regaining, flexion, extension and hyperextension
flexibility in an injured joint as well as aiding in resistance
training in order to regain lost muscle mass about the joint.
The system uses a pair of band holders that are rapidly
attached to and detached from the pair of aligned brace legs
of the brace, each holder having a receiver. An interchange-
able resistance band is removably received within each
receiver, either in the posterior or anterior position, held
therein by bulbous ends of the band. The resistance band
introduces static loading when the user is at rest as well as
dynamic loading when the user is utilizing the joint. A pulley
system can be used to offer the resistance band a medially
located pivot point so that the resistance band offers variable
resistance during dynamic loading.

18 Claims, 6 Drawing Sheets

BRACE WITH RESISTANCE BAND

This application is a Continuation-In-Part of U.S. patent application Ser. No. 17/945,193, filed on Sep. 15, 2022, which US application is incorporated herein by reference in its entirety.

BACKGROUND OF THE INVENTION

1. Field of the Invention

The present invention relates to a brace, such as a knee brace, that has a resistance band system that is rapidly removably attached thereto and removed therefrom without the need for any tools. The resistance band system has at least one laterally positioned removable resistance band that may pass over at least one pulley and that assists a patient who has undergone a knee procedure or otherwise suffered a knee injury in regaining extension and hyperextension flexibility as well as assist the patient in regaining lost muscle mass in the leg muscles about the knee.

2. Background of the Prior Art

When a patient has a knee procedure performed, the patient is fitted with a brace immediately thereafter in order to keep the operated upon knee and/or limb from being injured. A typical knee brace comprises an upper sleeve that encircles the patient's leg above the knee and a lower sleeve that encircles the patient's leg below the knee. A hinge system comprises one or more typical hinges that each connect the upper sleeve with the lower sleeve and allow articulation between the two sleeves about the knee, the hinges placed on opposing lateral (side) portions of the knee brace. The knee brace protects the patient by limiting the joint range of motion through a locking system at variable degrees as prescribed by their physician relative to their progression in the rehabilitation process. The locking system is part of the hinge system. The current brace models provide a range of motion anywhere from about −10 degrees (hyperextension) to 120 degrees of flexion. Elbow braces are structured similarly and function in similar fashion.

While current braces, which come in a variety of architectures, tend to be very good at protecting the knee (or elbow) and the surrounding limb from injury, current braces serve primarily as safety systems while the patient's joint heals during the immediate post-operative period. The brace does not address the rehabilitative process necessary for the patient.

One of the most important prerequisites to progressing through the knee rehabilitation process in the early stages of post-operation or post-injury to the knee is regaining the same extension or hyperextension on the knee similar to the contralateral side. Every step an individual with a healthy knee takes, requires the knee to hyperextend, or "lockout." Without the ability to do this, many issues can arise in a person's gate such as causing overuse injuries through compensation of the healthy knee as well as developing a limp due to the repaired knee's inability to function in a similar manner to the function of the person's healthy knee. There are known techniques to "stretch" the knee joint back out to a normal level of hyperextension, but such techniques are considered by many to be very primitive and somewhat barbaric as they place stresses on the knee joint, with little, if any, quantifiable loading measures that can be used by medical personnel to track progress and effectiveness of the rehabilitation process. In many of the known techniques, forcing the knee to hyperextend requires intense, painful, physical therapy. An example of such a technique has a therapist press down on the knee joint while the patient sits upright on a bench with the patient's leg extended. Another technique has the patient prop his or her foot up while seated and a belt strap or other tether is placed around the knee between the seat and the object the foot is propped up on. The therapist then tightens the strap down to force the knee to straighten, or lock out, with the patient being forced to stay in that position for a specified period of time to maintain the tension being applied by the strap. Another technique has the patient laying supine on a table with his or her feet hanging off the table with the therapist hanging a weight off of the patient's foot in order to force the knee to hyperextend. The patient is forced to stay in this relatively painful position for a specified period of time to hold the stretch being produced by the weight.

At some point during the rehabilitation process, the patient needs to engage in resistance training in order to reverse the muscle atrophy experienced by the leg muscles post-surgery. Typically, the patient engages in open-chain kinetic exercises using appropriate open-chain exercise machines. During this phase of rehab, the patient must be carefully monitored in order to avoid any sheering or other damage to the joint.

Conventional open-chain machines, such as leg curl or extension machines, do a great job of isolating the muscles around the joint, but force the upper portion of the limb above the joint to be fixated against a seat or pad. The machine then applies resistance to the most distal point of the lower limb away from the pivot point of the joint (typically around the ankle). Unfortunately, this process can cause a significant sheer effect on the knee, potentially causing reinjury to the knee, requiring further surgical intervention. Other muscle strengthening techniques are available but are relatively low impact and non-invasive in comparison to the machines, so that muscle mass regeneration takes significantly longer compared to using the open-chain machines.

What is needed is a device that assists a patient that has undergone a knee procedure in the post-operative rehabilitation phase which addresses the above stated shortcomings found in the art. Such a device must assist the patient in being able to gain extension and hyperextension flexibility from the knee. Additionally, such a device must be able to assist the patient in regaining leg muscle mass that may have been lost to atrophy post-surgery (and possibly pre-surgery). Such a device must minimize the risk of injury to the patient during device usage. Such a device must perform its tasks in a readily quantifiable manner so that the patient's therapists can monitor and adjust rehabilitation progress as needed.

SUMMARY OF THE INVENTION

In my U.S. Pat. No. 11,253,405, issued on Feb. 24, 2024, and U.S. Pat. No. 10,966,854, issued on Apr. 6, 2021, as well as currently pending U.S. patent application Ser. No. 17/945, 193, filed on Sep. 15, 2022, and each incorporated herein by reference in their entirety, I addressed the aforementioned needs in the art by providing knee braces that assist a user in regaining extension and hyperextension flexibility in the knee, post-surgery or post injury, without undue pain or undue discomfort that is experienced using current rehabilitation techniques. Each of the braces assist the patient in regaining leg muscle mass lost due to the knee injury while reducing the potential for either anterior or posterior knee shear or other injury being occasioned upon the rehabilitating knee. Progression through the use of each of the braces is quantifiable to allow a therapist to control and monitor progress throughout the rehabilitation process. The brace attachment system operates during otherwise normal wearing of a protective knee brace by the user to help reduce the need to attend physical therapy sessions as often, thereby reducing the associated time and monetary costs. Each of my previous braces is of relatively simple design and construction, being produced using standard manufacturing techniques to make the device readily affordable to potential consumers for this type of system. The current invention continues to offer the benefits of my previous brace attachment systems disclosed in the previously mentioned patents and offers additional functionality that is beneficial to the user.

The brace with resistance band of the present invention is comprised of a brace that has an upper sleeve system of appropriate design that encircles an upper portion of a user limb and a lower sleeve system of appropriate design that encircles a lower portion of the user's limb, the sleeve systems being typical limb encircling members that may have a strap system to adjust the fitting and possibly the comfort level of the knee brace about the limb. A hinge system of appropriate design is attached to the upper sleeve system via a first brace leg and to the lower sleeve system via a second brace leg and allows pivotal articulation between the upper sleeve system and the lower sleeve system as is known in the art of braces. A first band holder has a first body member that has a first base leg and a first tine such that an open first band channel is formed therebetween and such that the first band channel receives the first brace leg such that once the first brace leg is so received, the first tine of the first band holder is pressed toward the first base leg by rotating a first thumb screw that rotatably passes through the first tine and is threadably received within the first base leg so as to squeeze the first brace leg therebetween and thereby friction hold the first band holder in position on the first brace leg (counter-rotation of the first thumb screw reverses this process). The first base leg is dog-leg in shape, such that the short section of this first base leg, the distal section, is angled away the articulation point of the brace with respect to the long leg section of the first base leg. A first receiver has a first open passage and is located on a one or both ends of the first band holder. A second band holder has a second body member that has a second base leg and a second tine such that an open second band channel is formed therebetween and such that the second band channel receives the second brace leg such that once the second brace leg is so received, the second tine of the second band holder is pressed toward the second base leg by rotating a second thumb screw that rotatably passes through the second tine and is threadably received within the second base leg so as to squeeze the second brace leg therebetween and thereby friction hold the second band holder in position on the second brace leg (counter-rotation of the second thumb screw reverses this process). The second base leg is dog-leg in shape, such that the short section of this second base leg, the distal section, is angled away the articulation point of the brace with respect to the long leg section of the second base leg. A second receiver has a second open passage and is located on one or both ends of the second band holder. A resistance band has a first bulbous end and a second bulbous end such that the resistance band passes through a first open passage on the first band holder and the aligned second open passage on the second band holder. The first bulbous end prevents the resistance band from being pulled out of the first open passage and the second bulbous end prevents the resistance band from being pulled out of the second open passage. Each first receiver has a first slit leading to the first open passage, the first slit allowing the resistance band to be inserted into and removed from the first open passage and each second receiver has a second slit leading to the fourth open passage, the second slit allowing the resistance band to be inserted into and removed from the second open passage. A third body member has a third base leg and a third tine such that an open pulley channel is formed therebetween and such that the pulley channel receives one of the brace legs such that once the particular brace leg is so received, the third tine is pressed toward the third base leg by rotating a third thumb screw that rotatably passes through the third tine and is threadably received within the third base leg so as to squeeze the brace leg therebetween and thereby friction hold the pulley system in position on the first brace leg or the second brace leg, (counter-rotation of the third thumb screw reverses this process). The third body member attached to the first brace leg or the second brace leg between the first band holder and the second band holder. A pulley is rotatably located on the third body member. An additional pulley system (third body member and pulley) can be used.

BRIEF DESCRIPTION OF THE DRAWINGS

Similar reference numerals refer to similar parts throughout the several views of the drawings.

DESCRIPTION OF THE PREFERRED EMBODIMENT

Figure 1:
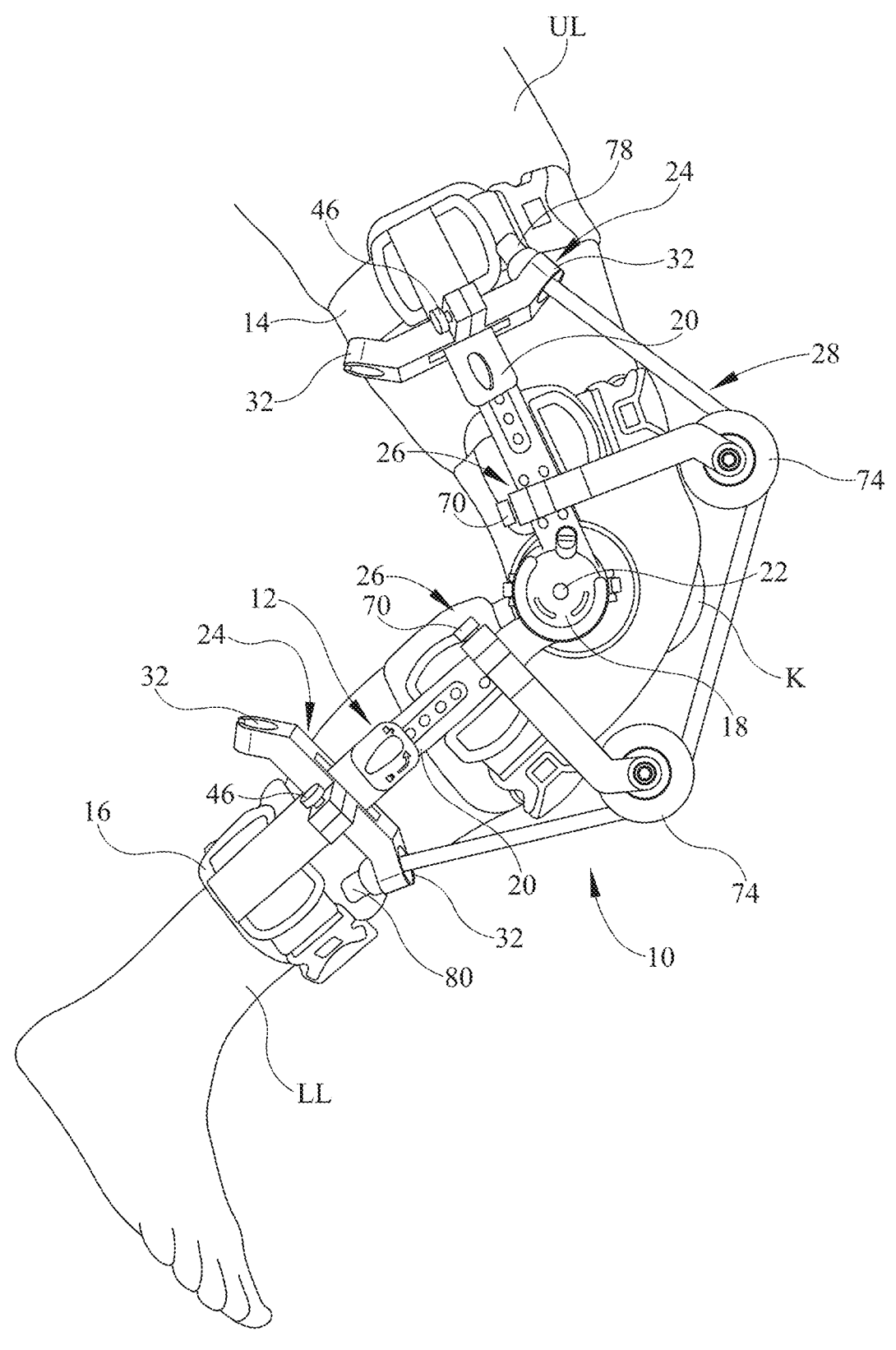
FIG. 1 is an environmental view of the brace with resistance band of the present invention with the resistance band being forward located and a user's knee being bent.

Referring now to the drawings, it is seen that the brace with resistance band of the present invention, generally denoted by reference numeral 10, is used in combination with a brace, such as an elbow brace, the illustrated knee brace 12 of any conventional type, including post-op, active/sport brace, etc. As seen, the typical brace 12 has an upper sleeve system 14 that encircles a user's upper leg UL and is secured thereat and a lower sleeve system 16 that encircles the user's lower leg LL. Appropriate sizing means may be located on each sleeve system 14 and 16 in order to assure a snug fit of the respective sleeve system about the respective portion of the user's leg. A hinge system 18 connects the upper sleeve system 14 and the lower sleeve system 16 via appropriate brace legs 20 and has a hinge point 22 that allows the upper sleeve system 14 to pivot with respect to the lower sleeve system 16 whenever the user walks or otherwise bends his or her knee K. As seen, the hinge system 18 is attached to a lateral side of the brace 12 and the same or similar components are located on the opposing lateral side of the brace 12. Of course, the specific details of both of the sleeve systems and the hinge system can vary between braces depending on the manufacturer of the particular brace and the specific accomplishments desired by the designers of the brace.

The brace with resistance band 10 is comprised of three main components, namely a pair of band holders 24, one or more pulley systems 26, and an interchangeable resistance band 28

Each band holder 24 is comprised of a band body 30 that has a band receiver 32 on one or both ends of the band body 30. The band body 30 has a band base leg 34 and a band tine 36 connected thereto such that a band channel 38 between the band base leg 34 and the band tine 36. As seen, the band channel 38 has a band well 40 formed therein. A threaded band opening 42 is located on the distal end of the band tine 36 while a corresponding threaded band boss 44 is located on the band base leg 34. A threaded band thumb screw 46 is received within the band opening 44 and rotated until the band thumb screw 46 is also received within the threaded band boss 44. Further rotation of the band thumb screw 46 causes the distal end of the band tine 36 to be pressed toward the band base leg 34 and thereby making the band channel 38 narrower. Counter-rotation of the band thumb screw 46 reverses this process.

Each band receiver 32 is a generally C-shaped member in cross-section and has a vertically disposed open passage 48 with a relatively narrow vertical slit 50 leading to the open passage 48.

Each pulley system 26 is comprised of a pulley body 52 that has pulley system leg 54 having a first end 56 and a second end 58. As seen, each pulley system leg 54 is dog-leg in shape. In this way, the longitudinal axis that passes through the longer leg section (the pulley leg section bearing the first end of the pulley leg system 54) of the pulley system leg 54 is offset at an obtuse angle (or a right angle) relative to the longitudinal axis that passes through the shorter leg section (the pulley leg section bearing the second end 58) of the pulley system leg 54. A pulley tine 60 is attached to the pulley system leg 54 medially of the first end 56 and the second end 58 of the pulley system leg 54 and extends toward the first end 56 of the pulley system leg 54. The pulley system leg 54 and the pulley tine 60 form a pulley channel 62 therebetween with its opening facing outwardly from the first end 56 of the pulley system leg 54. As seen, the pulley channel 62 has a pulley well 64 formed therein. A threaded pulley opening 66 is located on the distal end of the pulley tine 60 while a corresponding threaded pulley boss 68 is located on the pulley system leg 54. A threaded pulley thumb screw 70 is received within the pulley opening 66 and rotated until the pulley thumb screw 70 is also received within the pulley boss 68. Further rotation of the pulley thumb screw 70 causes the distal end of the pulley tine 60 to be pressed toward the pulley system leg 54 and thereby making the pulley channel 62 narrower. Counter-rotation of the pulley thumb screw 70 reverses this process.

A spindle 72 extends outwardly from the pulley system leg 54 proximate the second end 58 thereof. A low friction pulley 74 is rotatably received on the spindle 72 and held thereon via an appropriate screw 76.

The resistance band 28 has a first bulbous end 78 and a second bulbous end 80 and is made from an appropriate resilient material such as rubber.

In order to use the brace with resistance band 10 of the present invention, one of the band holders 24 is attached to the upper brace leg 20 of the brace 12 while the other band holder 24 is attached to the lower brace leg 20 of the brace

12 that is directly below the upper brace leg 20 to which the first band holder 24 has been attached. In order to attach each band holder 24 to its respective brace leg 20, the band holder 24 is positioned so that the edge of the brace leg 20 is located at the opening of the band channel 38 and then the band holder 24 is pressed against the brace leg 20 until the brace leg 20 is fully received within the band channel 38. The band tine 36 is sufficiently resilient to allow the brace leg 20 to so pass even with the band channel's side opening. Once the brace leg 20 is within the band channel 38, the brace leg 20 is moved until the brace leg 20 is seated within the band well 40. The band well 40 is sized and dimensioned so that the brace leg 20 sits snugly within the band well 40. Thereafter, the band thumb screw 46 is rotated so as to press the band tine 36 toward the band base leg 34 so as to narrow the band channel 38 and to squeeze the brace leg 20 within the band channel 38 between the band base leg 34 and band tine 36 and thereby firmly secure the band holder 24 onto the brace leg 20. If the band holder only has one band receiver, then each band holder is attached so that the band receiver of the upper band holder and the lower band holder are on the same side of the user, either both on the anterior side or both on the posterior side.

Figure 2:
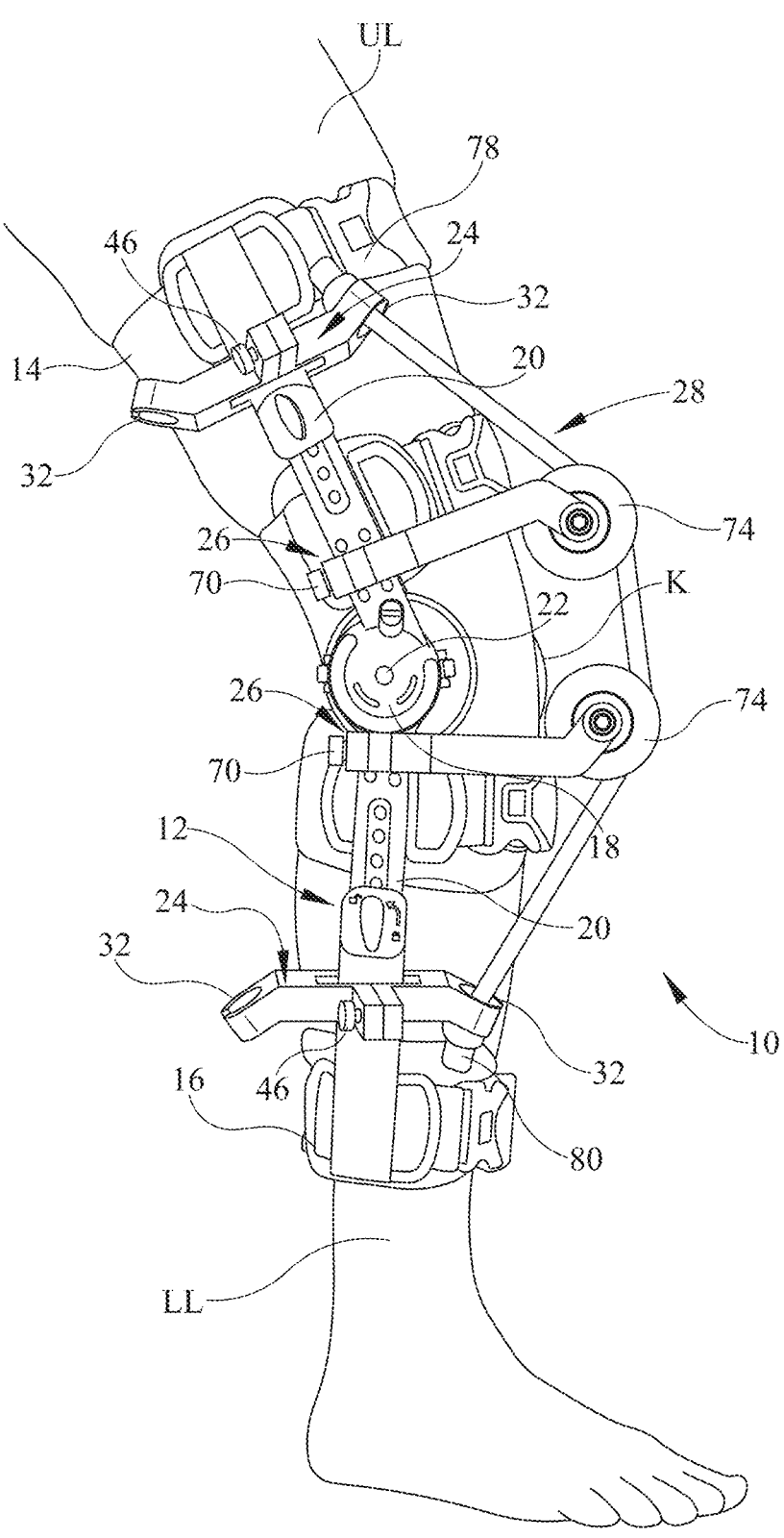
FIG. 2 is an environmental view of the brace with resistance band with the resistance band being forward located and a user's knee being relatively straightened.
Figure 3:
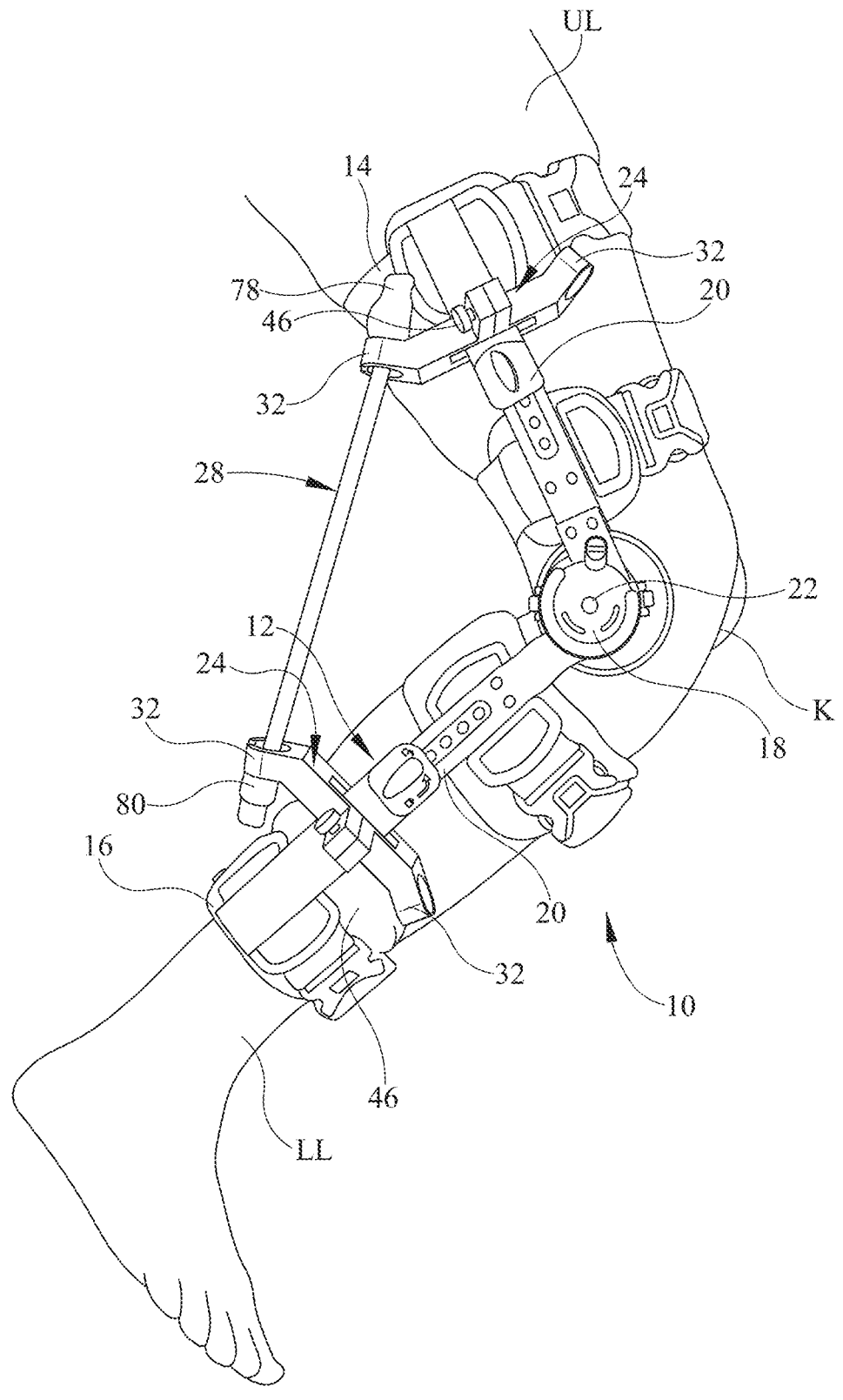
FIG. 3 is an environmental view of the brace with resistance band with the resistance band being rearward located and a user's knee being bent.
Figure 4:
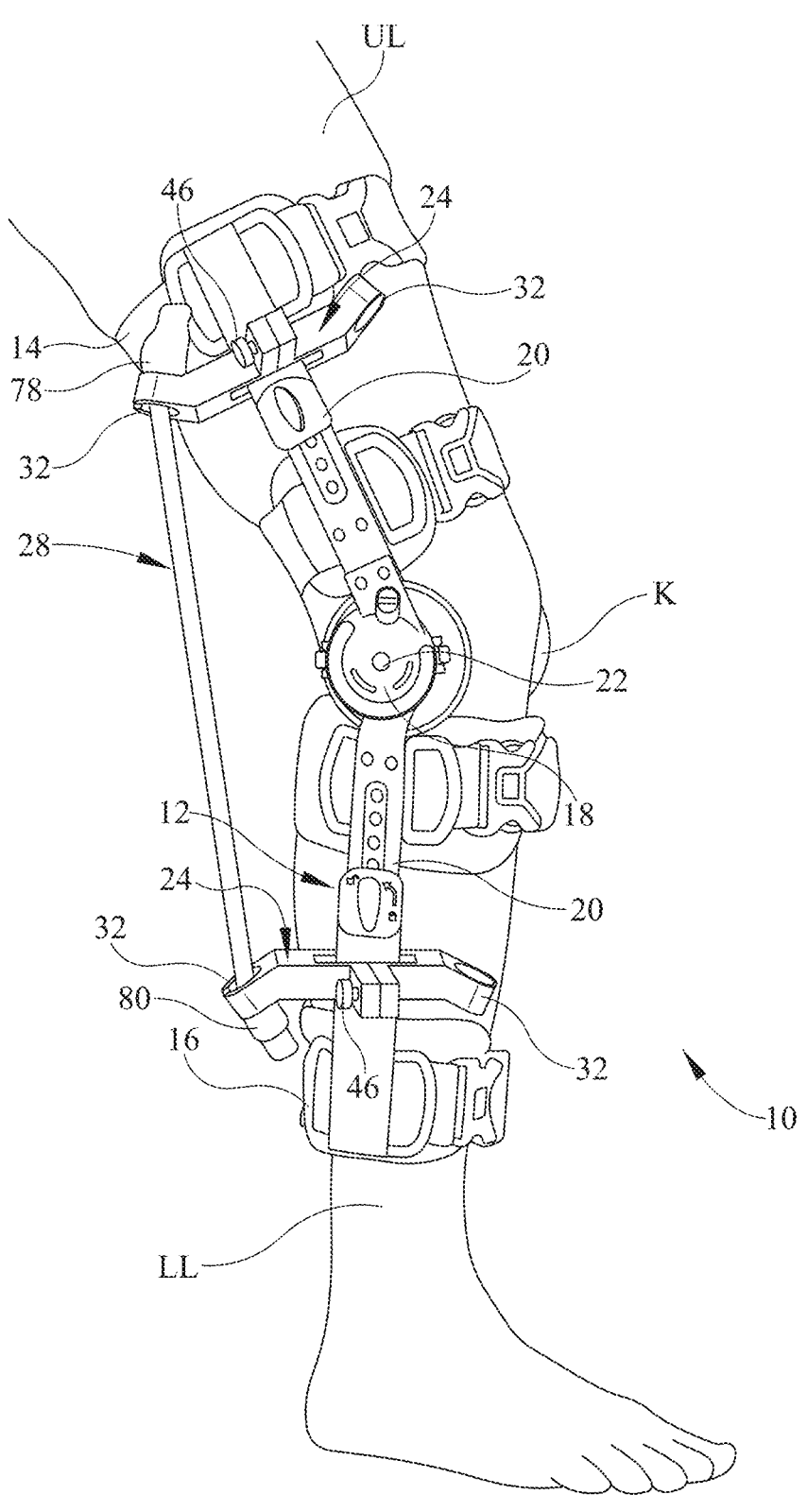
FIG. 4 is an environmental view of the brace with resistance band with the resistance band being rearward located and a user's knee being relatively straightened.
Figure 5:
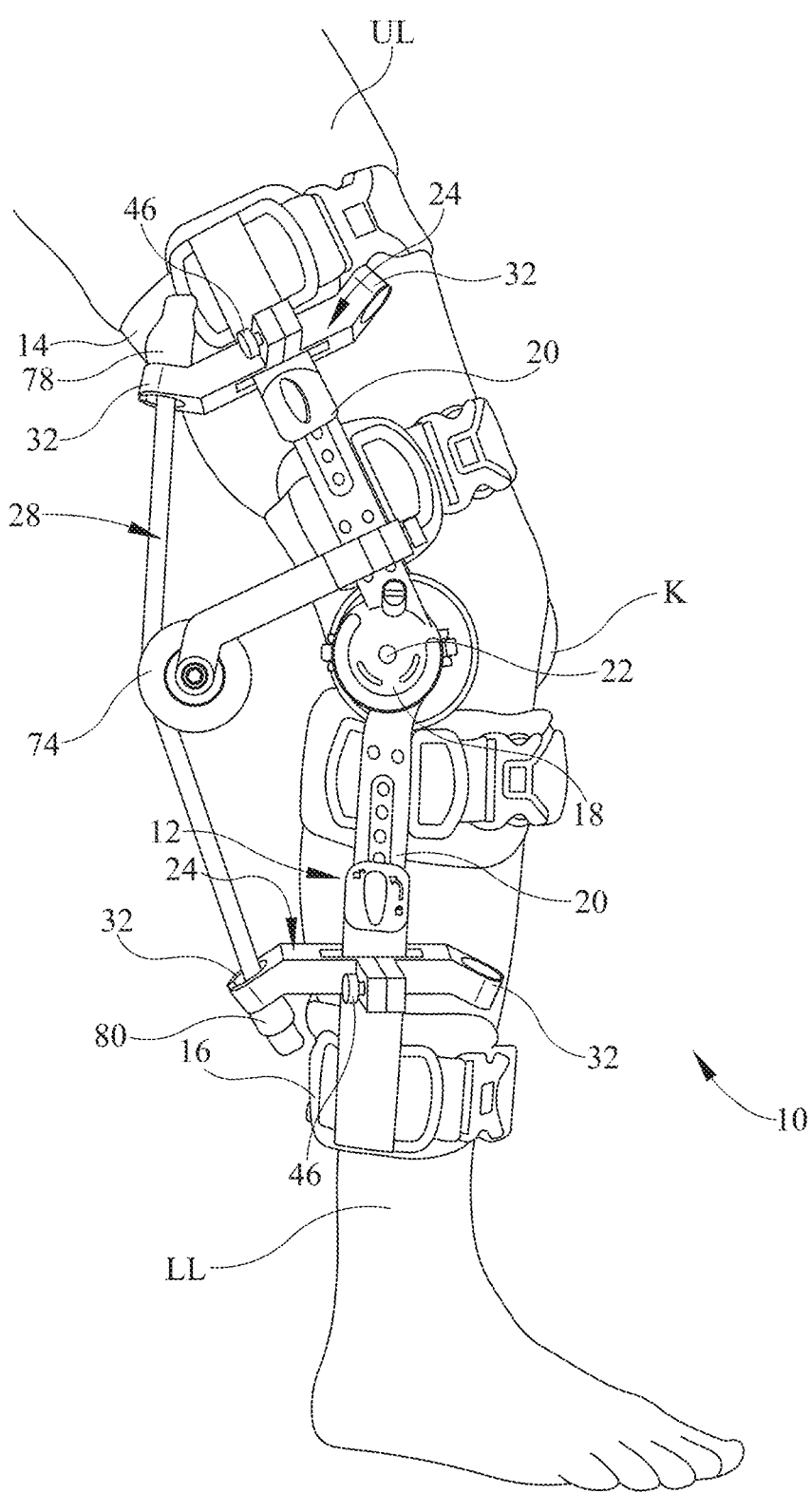
FIG. 5 is an environmental view of the brace with resistance band with the resistance band being rearward located and passing over a pulley.
Figure 6:
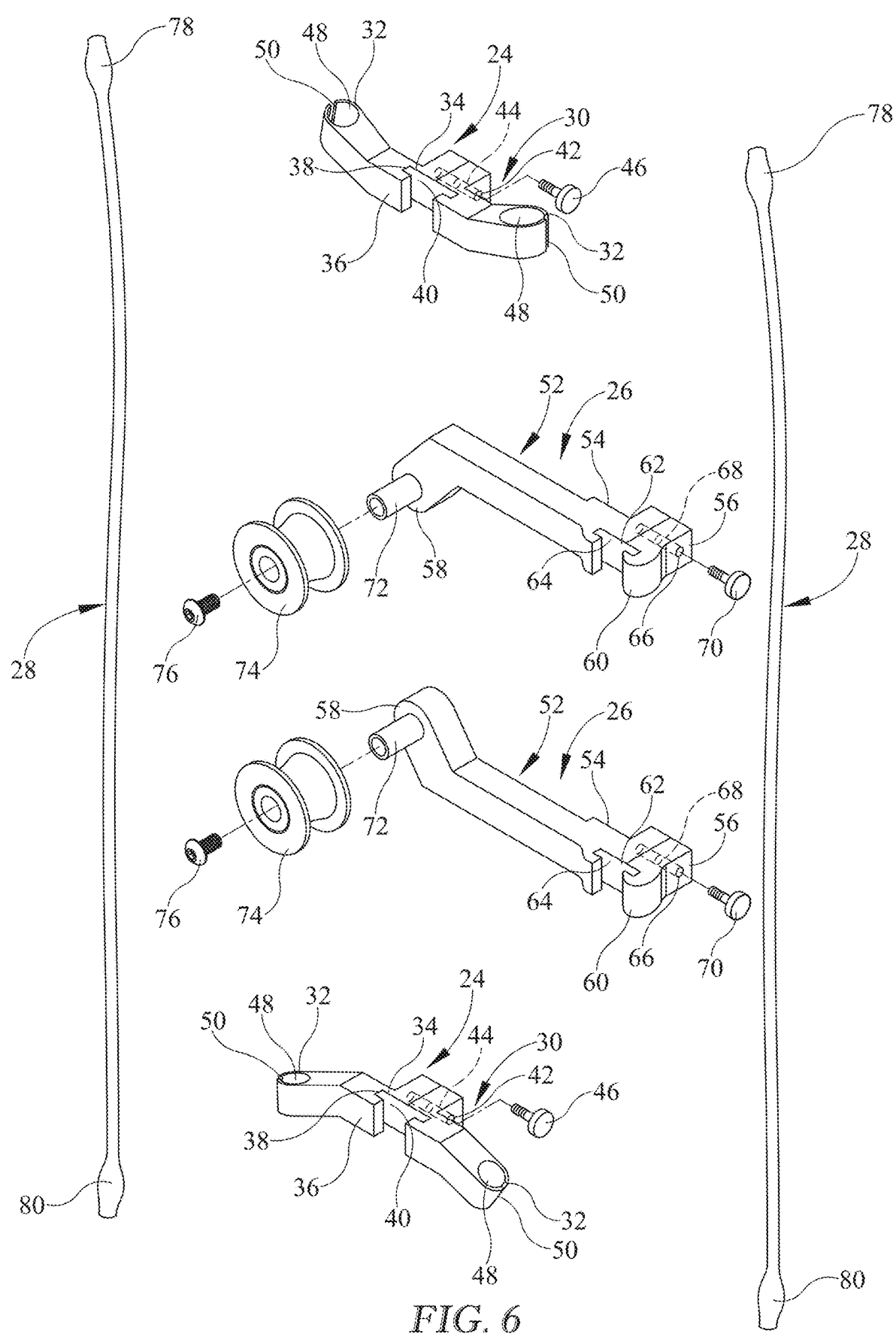
FIG. 6 is an exploded view of the various components of the brace with resistance band.

Thereafter, a pulley system 26 is attached to either the upper brace leg 20, the lower brace leg 20, or both (2 pulley systems 26 attached). In order to attach each pulley system 26 to its respective brace leg 20, the pulley system 26 is positioned so that the edge of the brace leg 20 is located at the opening of the pulley channel 62 and then the pulley system 26 is pressed against the brace leg 20 until the brace leg 20 is fully received within the pulley channel 62. Once the brace leg 20 is within the pulley channel 62, the brace leg 20 is moved until the brace leg 20 is seated within the pulley well 64. The pulley well 64 is sized and dimensioned so that the brace leg 20 sits snugly within the pulley well 64. Thereafter, the pulley thumb screw 70 is rotated so as to press the pulley tine 60 toward the pulley system leg 54 so as to narrow the pulley channel 62 and to squeeze the brace leg 20 within the pulley channel 62 between the pulley system leg 54 and pulley tine 60 and thereby firmly secure the pulley system 26 onto the brace leg 20. If more than one pulley system 26 is attached to the brace 12, then each pulley 74 must be on the same side of the user, either both on the anterior side or both on the posterior side (and on the same side of the band receivers if the band holder only has a single band receiver). As best seen in FIGS. 1 and 2, when the pulley systems 26 are installed, the dog-leg shaped pulley system legs 54 face toward one another. That is, the short section of each pulley system leg 54 are angled toward one another, or in other words, the short leg section of the pulley system leg 54 (the portion bearing the second end 58) that is installed above hinge point 22 faces downwardly while the short leg section of the pulley system leg 54 (the section bearing the second end 58) that is installed below hinge point 22 faces upwardly. The use of a dog-leg shape for each of the pulley system legs 54 allows for the use of shorter overall legs creating a more compact design of the overall device. Additionally, the use of inwardly directed dog-legged pulley system legs 54 helps reduce the stresses at the attachment points where the pulley system legs 54 are attached to their respective brace legs 20.

The attachment of the pulley system 26 is optional

A second brace with resistance band can be attached to the opposite side of the brace 12 (not illustrated)

A resistance band 28 having the desired level of resistance is selected and attached to the brace with resistance band 10 by passing a section of the resistance band 28 just below the first bulbous end 78 through either the slit 50 of the upper band holder 24 until the resistance band is fully within the open passage 48. Advantageously, the cross section of the slit 50 through which the resistance band 28 passes is slightly smaller than the cross section of the resistance band 28 at the area of insertion whenever the resistance band 28 is in a normally relaxed state so that a reasonable amount of force must be used to press the resistance band 28 through the slit 50 which then makes removal of the resistance band 28 from the open passage 48 require a reasonable amount of force. The resistance band is able to be stretched due to its resilient nature, in order to lower its cross section so as to allow the resistance band 28 to be able pass through the slit 50. Thereafter, the opposing end of the resistance band 28 is attached to the corresponding band receiver 32 in similar fashion so that a section of the resistance band 28 just about the second bulbous end 80 through the slit 50 on the lower band receiver 32 of the lower band holder 24. The bulbous ends 78 and 80 of the resistance band 28 (which are located on the outer side of their respective band holder 24—not between the two band holders 24) are sufficiently large so as to prevent the resistance band 28 from being pulled through the open passage 48 of the band receiver 32.

If one or more pulley systems 26 is attached to the brace 12, the resistance band 28 is placed onto each such pulley 74, which pretensions the resistance band 28.

The user can use the brace 12 in appropriate fashion such as via walking or running or simply flexing the knee K. The resistance is provided to the brace 12 via the resistance band 28. This resistance aids the knee K with either extension or hyperextension flexing as the patient is walking, during flexion of the knee K by loading the hamstring, and also during extension of the knee K by loading the quadriceps. The resistance band 28 creates static tension helping hyperextend the knee K while the brace 12 is on the leg and unlocked to about –10 degrees, which allows the patient to prop the leg up in a similar fashion as conventional rehab, but with more incremental resistance options. If additional resistance is needed during rehab progression, then either a second resistance band 28 can be added to the device as described above, or the initial resistance band 28 is detached and a new more resistant (or less resistant) resistance band 28 is attached, such resistance band 28 swap out being relatively quick and easy. If the pulley system 26 is being used, then the resistance band 28 is removed from one or both of the pulleys 74 (if two pulleys 74 are being used) in order to decrease resistance of the resistance band 28, or the resistance band 28 is placed onto the pulleys 74 if not already placed thereon, in order to increase resistance of the resistance band 28 Additionally, if the user is in a position so as to only have the one resistance band 28, the user can change the relative position of the two band holders 24 so that moving the band holders 24 closer toward one another decreases the resistance of the resistance band 28 and moving the band holders 24 farther away from each other increases the resistance of the resistance band 28. Movement of one or both of the band holders 24 to so achieve this change of resistance is relatively simple. Simply counter-rotate the band thumb screw until the pressure on the brace leg 20 by the band base leg 34 and the band tine 36 is sufficiently low so as to allow the band holder to slide either up or down along its brace leg 20. Once the band holder 24 is in its desired new position, the band thumb screw 46 is once again rotated to tighten the band holder 24 onto it brace leg 20. If pulleys 74 are used, the pulleys 74 rotate as the resistance band 28 passes along them making for a smooth motion.

Removal of the band holders 24 is similarly easy. Simply counter-rotate the band holder's thumb screw 46 until the brace leg 20 can slide out of the band channel 38. In order to remove the pulley system, counter-rotate the pulley thumb screw 70 until the brace leg 20 can slide out of the pulley channel 62.

Each of the components of the brace with resistance band 10 of the present invention, with the exception of the resistance band 28, is made from an appropriate strong and sturdy material such as metal, plastic, composite, etc., and may have appropriate friction reducing properties It should be evident; the current system can be dimensionally adjusted for use about a person's upper limbs and function as an elbow brace in substantially similar fashion.

While the invention has been particularly shown and described with reference to an embodiment thereof, it will be appreciated by those skilled in the art that various changes in form and detail may be made without departing from the spirit and scope of the invention.

We claim:

1. A rehabilitation system attached to a brace, the brace having an upper sleeve system that is adapted to encircle an upper portion of a user's limb and a lower sleeve that is adapted to encircle the lower portion of the user's limb such that a hinge system is attached to the upper sleeve system and to the lower sleeve system via a first brace leg and a second brace leg, the first brace leg attaching the hinge system with the upper sleeve system and the second brace leg attaching the hinge system with the lower sleeve system, the hinge system allows pivotal articulation between the upper sleeve system and the lower sleeve system, the rehabilitation system comprising:

a first band holder having a first body member that has a first base leg and a first tine such that an open first band channel is formed therebetween and such that the first band channel is adapted to receive the first brace leg such that once the first brace leg is so received, the first tine of the first band holder is pressed toward the first base leg so as to squeeze the first brace leg therebetween and thereby friction hold the first band holder in position on the first brace leg, the first base leg having a first long leg section and a first short leg section, the first short leg section angled away the hinge system from the first long leg section;

a first receiver having a first open passage located on a first end of the first band holder;

a second band holder having a second body member that has a second base leg and a second tine such that an open second band channel is formed therebetween and such that the second band channel is adapted to receive the second brace leg such that once the second brace leg is so received, the second tine of the second band holder is pressed toward the second base leg so as to squeeze the second brace leg therebetween and thereby friction hold the second band holder in position on the second brace leg, the second base leg having a second long leg section and a second short leg section, the second short leg section angled away the hinge system from the second long leg section;

a second receiver having a second open passage located on a third end of the second band holder; and a resistance band having a first bulbous end and a second bulbous end such that the resistance band passes through the first open passage and the second open passage such that the first bulbous end prevents the resistance band from being pulled out of the first open passage and the second bulbous end prevents the resistance band from being pulled out of the second open passage.

2. The rehabilitation system as in claim 1 wherein the first receiver has a first slit leading to the first open passage, the first slit allowing the resistance band to be inserted into and removed from the first open passage and the second receiver has a second slit leading to the second open passage, the second slit allowing the resistance band to be inserted into and removed from the second open passage.

3. The rehabilitation system as in claim 1 further comprising:

a pulley system having a third body member that has a third base leg and a third tine such that an open pulley channel is formed therebetween and such that the pulley channel is adapted to receive either the first brace leg or the second brace leg such that once the first brace leg or the second brace leg is so received, the third tine is pressed toward the third base leg so as to squeeze the first brace leg or the second brace leg therebetween and thereby friction hold the pulley system in position on the first brace leg or the second brace leg, the third body member attached to the first brace leg or the second brace leg between the first band holder and the second band holder; and a pulley rotatably located on the third body member.

4. The rehabilitation system as in claim 1 in combination with the brace.

5. The rehabilitation system as in claim 4 wherein the first receiver has a first slit leading to the first open passage, the first slit allowing the resistance band to be inserted into and removed from the first open passage and the second receiver has a second slit leading to the second open passage, the second slit allowing the resistance band to be inserted into and removed from the second open passage.

6. The rehabilitation system as in claim 4 further comprising:

a pulley system having a third body member that has a third base leg and a third tine such that an open pulley channel is formed therebetween and such that the pulley channel is adapted to receive either the first brace leg or the second brace leg such that once the first brace leg or the second brace leg is so received, the third tine is pressed toward the third base leg so as to squeeze the first brace leg or the second brace leg therebetween and thereby friction hold the pulley system in position on the first brace leg or the second brace leg, the third body member attached to the first brace leg or the second brace leg between the first band holder and the second band holder; and a pulley rotatably located on the third body member.

7. A rehabilitation system attached to a brace, the brace having an upper sleeve system that is adapted to encircle an upper portion of a user's limb and a lower sleeve that is adapted to encircle the lower portion of the user's limb such that a hinge system is attached to the upper sleeve system and to the lower sleeve system via a first brace leg and a second brace leg, the first brace leg attaching the hinge system with the upper sleeve system and the second brace leg attaching the hinge system with the lower sleeve system, the hinge system allows pivotal articulation between the upper sleeve system and the lower sleeve system, the rehabilitation system comprising:

a first band holder having a first body member that has a first base leg and a first tine such that an open first band channel is formed therebetween and such that the first band channel is adapted to receive the first brace leg such that once the first brace leg is so received, the first tine of the first band holder is pressed toward the first base leg so as to squeeze the first brace leg therebetween and thereby friction hold the first band holder in position on the first brace leg, the first base leg having a first long leg section and a first short leg section, the first short leg section angled away the hinge system from the first long leg section;

a first receiver having a first open passage located on a first end of the first band holder;

a second receiver having a second open passage located on an opposing second end of the second band holder;

a second band holder having a second body member that has a second base leg and a second tine such that an open second band channel is formed therebetween and such that the second band channel is adapted to receive the second brace leg such that once the second brace leg is so received, the second tine of the second band holder is pressed toward the second base leg so as to squeeze the second brace leg therebetween and thereby friction hold the second band holder in position on the second brace leg, the second base leg having a second long leg section and a second short leg section, the second short leg section angled away the hinge system from the second long leg section;

a third receiver having a third open passage located on a third end of the second band holder;

a fourth receiver having a fourth open passage located on an opposing fourth end of the second band holder; and a resistance band having a first bulbous end and a second bulbous end such that the resistance band passes through the first open passage and the third open passage or through the second open passage and the fourth open passage such that the first bulbous end prevents the resistance band from being pulled out of the first open passage or the second open passage and the second bulbous end prevents the resistance band from being pulled out of the third open passage or the fourth open passage.

8. The rehabilitation system as in claim 7 wherein the first receiver has a first slit leading to the first open passage, the first slit allowing the resistance band to be inserted into and removed from the first open passage, the second receiver has a second slit leading to the second open passage, the second slit allowing the resistance band to be inserted into and removed from the second open passage, the third receiver has a third slit leading to the third open passage, the third slit allowing the resistance band to be inserted into and removed from the third open passage and the fourth receiver has a fourth slit leading to the fourth open passage, the fourth slit allowing the resistance band to be inserted into and removed from the fourth open passage.

9. The rehabilitation system as in claim 7 further comprising:

a pulley system having a third body member that has a third base leg and a third tine such that an open pulley channel is formed therebetween and such that the pulley channel is adapted to receive either the first brace leg or the second brace leg such that once the first brace leg or the second brace leg is so received, the third tine is pressed toward the third base leg so as to squeeze the first brace leg or the second brace leg therebetween and thereby friction hold the pulley system in position on the first brace leg or the second brace leg, the third body member attached to the first brace leg or the second brace leg between the first band holder and the second band holder; and a pulley rotatably located on the third body member.

10. The rehabilitation system as in claim 7 in combination with the brace.

11. The rehabilitation system as in claim 10 wherein the first receiver has a first slit leading to the first open passage, the first slit allowing the resistance band to be inserted into and removed from the first open passage, the second receiver has a second slit leading to the second open passage, the second slit allowing the resistance band to be inserted into and removed from the second open passage, the third receiver has a third slit leading to the third open passage, the third slit allowing the resistance band to be inserted into and removed from the third open passage and the fourth receiver has a fourth slit leading to the second open passage, the fourth slit allowing the resistance band to be inserted into and removed from the fourth open passage.

12. The rehabilitation system as in claim 10 further comprising:

a pulley system having a third body member that has a third base leg and a third tine such that an open pulley channel is formed therebetween and such that the pulley channel is adapted to receive either the first brace leg or the second brace leg such that once the first brace leg or the second brace leg is so received, the third tine is pressed toward the third base leg so as to squeeze the first brace leg or the second brace leg therebetween and thereby friction hold the pulley system in position on the first brace leg or the second brace leg, the third body member attached to the first brace leg or the second brace leg between the first band holder and the second band holder; and a pulley rotatably located on the third body member.

13. A rehabilitation system attached to a brace, the brace having an upper sleeve system that is adapted to encircle an upper portion of a user's limb and a lower sleeve that is adapted to encircle the lower portion of the user's limb such that a hinge system is attached to the upper sleeve system and to the lower sleeve system via a first brace leg and a second brace leg, the first brace leg attaching the hinge system with the upper sleeve system and the second brace leg attaching the hinge system with the lower sleeve system, the hinge system allows pivotal articulation between the upper sleeve system and the lower sleeve system, the rehabilitation system comprising:

a first band holder having a first body member that has a first base leg and a first tine such that an open first band channel is formed therebetween and such that the first band channel is adapted to receive the first brace leg such that once the first brace leg is so received, the first tine of the first band holder is pressed toward the first base leg by rotating a first thumb screw that rotatably passes through the first tine and is threadably received within the first base leg so as to squeeze the first brace leg therebetween and thereby friction hold the first band holder in position on the first brace leg, the first base leg being having a first long leg section and a first short leg section, the first short leg section angled away the hinge system from the first long leg section;

a first receiver having a first open passage located on a first end of the first band holder;

a second band holder having a second body member that has a second base leg and a second tine such that an open second band channel is formed therebetween and such that the second band channel is adapted to receive the second brace leg such that once the second brace leg is so received, the second tine of the second band holder is pressed toward the second base leg by rotating a second thumb screw that rotatably passes through the second tine and is threadably received within the second base leg so as to squeeze the second brace leg therebetween and thereby friction hold the second band holder in position on the second brace leg, the second base leg having a second long leg section and a second short leg section, the second short leg section angled away the hinge system from the second long leg section;

a second receiver having a second open passage located on a second end of the second band holder; and a resistance band having a first bulbous end and a second bulbous end such that the resistance band passes through the first open passage and the second open passage such that the first bulbous end prevents the resistance band from being pulled out of the first open passage and the second bulbous end prevents the resistance band from being pulled out of the second open passage.

14. The rehabilitation system as in claim 13 wherein the first receiver has a first slit leading to the first open passage, the first slit allowing the resistance band to be inserted into and removed from the first open passage and the second receiver has a second slit leading to the second open passage, the second slit allowing the resistance band to be inserted into and removed from the second open passage.

15. The rehabilitation system as in claim 13 further comprising:

a pulley system having a third body member that has a third base leg and a third tine such that an open pulley channel is formed therebetween and such that the pulley channel is adapted to receive either the first brace leg or the second brace leg such that once the first brace leg or the second brace leg is so received, the third tine is pressed toward the third base leg by rotating a third thumb screw that rotatably passes through the third tine and is threadably received within the third base leg so as to squeeze the first brace leg or the second brace leg therebetween and thereby friction hold the pulley system in position on the first brace leg or the second brace leg, the third body member attached to the first brace leg or the second brace leg between the first band holder and the second band holder; and a pulley rotatably located on the third body member.

16. The rehabilitation system as in claim 13 in combination with the brace.

17. The rehabilitation system as in claim 16 wherein the first receiver has a first slit leading to the first open passage, the first slit allowing the resistance band to be inserted into and removed from the first open passage and the second receiver has a second slit leading to the second open passage, the second slit allowing the resistance band to be inserted into and removed from the second open passage.

18. The rehabilitation system as in claim 16 further comprising:

a pulley system having a third body member that has a third base leg and a third tine such that an open pulley channel is formed therebetween and such that the pulley channel is adapted to receive either the first brace leg or the second brace leg such that once the first brace leg or the second brace leg is so received, the third tine is pressed toward the third base leg by rotating a third thumb screw that rotatably passes through the third tine and is threadably received within the third base leg so as to squeeze the first brace leg or the second brace leg therebetween and thereby friction hold the pulley system in position on the first brace leg or the second brace leg, the third body member attached to the first brace leg or the second brace leg between the first band holder and the second band holder; and a pulley rotatably located on the third body member.

\* \* \* \* \*